United States Patent
Power et al.

(10) Patent No.: US 9,968,759 B2
(45) Date of Patent: May 15, 2018

(54) DEVICES AND METHODS FOR PERFUSING AN ORGAN

(71) Applicant: Osprey Medical, Inc., Minnetonka, MN (US)

(72) Inventors: John Melmouth Power, Williamstown (AU); Mark L. Mathis, Fremont, CA (US); David Martin Kaye, Beaumaris (AU); Adam Lucas Bilney, Wy Yung (AU)

(73) Assignee: OSPREY MEDICAL. INC., Minnetonka, MN (US)

( * ) Notice: Subject to any disclaimer, the term of this patent is extended or adjusted under 35 U.S.C. 154(b) by 0 days. days.

(21) Appl. No.: 14/882,139

(22) Filed: Oct. 13, 2015

(65) Prior Publication Data
US 2016/0030714 A1    Feb. 4, 2016

Related U.S. Application Data

(63) Continuation of application No. 13/892,925, filed on May 13, 2013, which is a continuation of application (Continued)

(51) Int. Cl.
*A61M 25/01*    (2006.01)
*A61M 25/09*    (2006.01)
(Continued)

(52) U.S. Cl.
CPC ............... *A61M 25/01* (2013.01); *A61F 2/82* (2013.01); *A61M 25/09* (2013.01); *A61M 25/10* (2013.01);
(Continued)

(58) Field of Classification Search
CPC ...... A61M 25/04; A61M 25/09; A61M 25/10; A61M 25/1011; A61M 2025/0197;
(Continued)

(56) References Cited

U.S. PATENT DOCUMENTS

| 4,795,447 A | 1/1989 | Dodson |
| 5,071,407 A | 12/1991 | Termin et al. |

(Continued)

FOREIGN PATENT DOCUMENTS

| EP | 0518704 | 12/1992 |
| EP | 0835673 | 4/1998 |

(Continued)

OTHER PUBLICATIONS

PCT International Search Report and Written Opinion in International Application PCT/AU2006/001234, dated Nov. 8, 2006, 7 pgs.

*Primary Examiner* — Bhisma Mehta
*Assistant Examiner* — Larry R Wilson

(57) ABSTRACT

The present invention provides devices and methods for use in the perfusion of organs and anatomical regions. In one aspect the present method provides a percutaneously deliverable device for supporting a vessel in a human or animal subject including means for supporting the vessel during delivery of a fluid thereto or collection of a fluid therefrom. In another aspect the invention provides a method for delivery or collection of a fluid to or from an organ or anatomical region in a human or animal subject, the method including the step of supporting a vessel associated with the organ or anatomical region. The devices and methods may be used to deliver, remove or recirculate a therapeutic agent to an organ or anatomical region.

13 Claims, 7 Drawing Sheets

Related U.S. Application Data

No. 11/996,416, filed as application No. PCT/AU2006/001234 on Aug. 25, 2006, now abandoned.

(60) Provisional application No. 60/753,478, filed on Dec. 22, 2005, provisional application No. 60/711,298, filed on Aug. 25, 2005.

(51) Int. Cl.
*A61F 2/82* (2013.01)
*A61M 29/02* (2006.01)
*A61M 25/10* (2013.01)

(52) U.S. Cl.
CPC ... *A61M 29/02* (2013.01); *A61M 2025/09183* (2013.01); *A61M 2025/1052* (2013.01)

(58) Field of Classification Search
CPC ........... A61M 2025/09183; A61M 2025/1052; A61M 29/02; A61M 3/0291; A61F 2/82; A61F 2002/825
See application file for complete search history.

(56) References Cited

U.S. PATENT DOCUMENTS

| | | |
|---|---|---|
| 5,135,517 A | 8/1992 | McCoy |
| 5,193,533 A | 3/1993 | Body et al. |
| 5,354,310 A | 10/1994 | Garnic et al. |
| 5,378,239 A | 1/1995 | Termin et al. |
| 5,441,516 A | 8/1995 | Wang et al. |
| 5,456,667 A | 10/1995 | Ham et al. |
| 5,509,900 A * | 4/1996 | Kirkman ........... A61M 25/0082 604/104 |
| 5,713,853 A | 2/1998 | Clark et al. |
| 5,954,742 A | 9/1999 | Osypka |
| 5,957,899 A | 9/1999 | Spears et al. |
| 5,957,900 A | 9/1999 | Ouchi |
| 6,135,991 A | 10/2000 | Muni et al. |
| 6,270,490 B1 * | 8/2001 | Hahnen ............... A61M 1/3666 604/104 |
| 6,283,940 B1 | 9/2001 | Mulholland |
| 6,295,990 B1 | 10/2001 | Lewis et al. |
| 6,340,356 B1 | 1/2002 | Navia et al. |
| 6,508,777 B1 | 1/2003 | Macoviak et al. |
| 6,554,819 B2 * | 4/2003 | Reich ................. A61M 1/3653 604/4.01 |
| 6,676,692 B2 | 1/2004 | Rabkin et al. |
| 6,726,651 B1 | 4/2004 | Robinson et al. |
| 7,211,073 B2 | 5/2007 | Fitzgerald et al. |
| 7,300,429 B2 | 11/2007 | Fitzgerald et al. |
| 7,331,922 B2 | 2/2008 | Mohl |
| 2002/0099254 A1 | 7/2002 | Movahed |
| 2004/0193206 A1 | 9/2004 | Gerberding et al. |
| 2006/0200191 A1 | 9/2006 | Zadno-Azizi |
| 2008/0021314 A1 | 1/2008 | Movahed |
| 2009/0018526 A1 | 1/2009 | Power et al. |
| 2013/0253629 A1 | 9/2013 | Power et al. |

FOREIGN PATENT DOCUMENTS

| | | |
|---|---|---|
| GB | 2264236 | 8/1993 |
| WO | WO 2003/080166 | 10/2003 |
| WO | WO 2005/082440 | 9/2005 |

* cited by examiner

DEVICES AND METHODS FOR PERFUSING AN ORGAN

CROSS REFERENCE TO RELATED APPLICATIONS

This application is a continuation of U.S. patent application Ser. No. 13/892,925, entitled DEVICES AND METHODS FOR PERFUSING AN ORGAN, filed May 13, 2013; which is a continuation of U.S. patent application Ser. No. 11/996,416, filed Jun. 10, 2008; which is National Stage application of PCT/AU2006/001234 filed Aug. 25, 2006; which claims priority to and benefit of U.S. Provisional Patent Application No. 60/753,478, filed Dec. 22, 2005; and U.S. Provisional Patent Application No. 60/711,298, filed Aug. 25, 2005; the disclosures of which are hereby incorporated by reference herein.

FIELD OF THE INVENTION

The present invention relates to a support device for supporting a vessel of a human or animal subject. The support device can be used, for example, during procedures in which a fluid is collected from an organ or anatomical region via an associated blood vessel.

BACKGROUND TO THE INVENTION

Many therapeutic procedures can be performed percutaneously. Such procedures include investigative and diagnostic methods as well as medical and surgical treatments. Percutaneous techniques are advantageous because they are minimally invasive, and therefore present a reduced risk to the patient when compared with invasive surgeries requiring open access to tissues within the patient's body.

Catheters and sheaths are typically used to access internal sites by entering the patient's body through an incision or other entry point to the peripheral vasculature and navigating through the torturous paths of the vascular system to the target site. Tools, cameras illumination sources and transducers can be deployed through the catheters and sheaths enabling a physician to inspect the site, take biopsies, implant devices, repair damage and perform numerous other tasks often on an outpatient basis.

Minimally invasive percutaneous approaches have also presented an opportunity for localized delivery of therapeutic agents. Localization facilitates improved treatment since the agent may be delivered directly to a target site, (for example, an organ) thereby avoiding "first pass" degradation in the liver. The agent may therefore exhibit an improved therapeutic effect when compared with the same agent administered orally, intravenously or via the intramuscular route. Moreover, where the therapeutic agent has benefit to the target site but is likely to be toxic to other organs or tissues, localized delivery can minimize the exposure and hence the risk presented to cells in other parts of the body. An example is where a cytotoxic drug is to be delivered to a cancerous organ, but it is desired to minimize or prevent exposure of healthy organs to the drug.

Various devices and methods to facilitate the percutaneous delivery and collection of fluids to organs and tissues of the human body have been described in the art. Typically, these devices and methods include a first catheter to deliver a fluid to an organ or tissue and a second catheter to collect fluid exiting the organ or tissue. The collected fluid may be returned to the organ, or discarded as waste outside the body.

While devices and methods of the prior art appear to address the theoretical requirements of percutaneous delivery and collection of fluids, Applicant has found that they are of little practical use in the clinic. In particular, difficulties are encountered in maintaining sufficient flow rates of fluid through a collection catheter. As will be appreciated by the skilled person, where a collection catheter is positioned in a vein, venous pooling, tissue damage and possible death of the subject can result from low flow rates. Low flow rates via a collection catheter may also severely limit the ability to deliver the therapeutic agent via a delivery catheter given that in order to maintain fluid balance the volume of fluid entering and exiting should be substantially equal.

Applicants have identified a further problem with devices and methods of the prior art in that damage to vessel walls may also be noted after catheterization of vessels. Where the catheter is a collection catheter, partial or complete occlusion is sometimes observed during use. Yet a further problem exists in that catheters often move from the position in which they are deployed.

It is an aspect of the present invention to overcome or alleviate a problem of the prior art by providing devices and methods capable of maintaining the flow of fluid via the collection catheter. The methods and devices may also minimize vessel wall damage, occlusion of the catheter lumen, and movement of a catheter after placement.

The discussion of documents, acts, materials, devices, articles and the like is included in this specification solely for the purpose of providing a context for the present invention. It is not suggested or represented that any or all of these matters formed part of the prior art base or were common general knowledge in the field relevant to the present invention as it existed before the priority date of each claim of this application.

SUMMARY OF THE INVENTION

In one aspect the present invention provides a percutaneously deliverable device for supporting a vessel in a human or animal subject including means for supporting the vessel during delivery of a fluid thereto or collection of fluid therefrom. Without wishing to be limited by theory, Applicant proposes that collapse of the vessel wall is at least partly responsible for the low flow rates that are problematic in the percutaneous collection of fluids from an organ or tissue of the body. The support devices described herein have the effect of maintaining patency of the vessel via which fluid is being collected, while also preventing collision of the collection catheter with the vessel wall. Maintenance of patency of the collection vessel allows for useful flow rates to be established, thereby reducing the risk of venous pooling. Where the invention further includes delivery of a fluid to a tissue or organ, flow rates of the fluid into the tissue or organ are also improved.

In one embodiment of the method the means for supporting the vessel is capable of maintaining patency of the vessel during delivery of the fluid thereto or collection of the fluid therefrom. Movement of fluids into and out of a vessel can cause deformations in the wall of the vessel leading to collapse. The collapse of the vessel wall can lead to complete obstruction of the vessel thereby preventing any further flow of fluid. In particular drawing fluid out of a vessel during collection can lead to a decrease in pressure in the vessel which in turn leads to vessel collapse. Vessels have a normal range of pressures under which they function in the body. The normal range is that noted in a healthy subject, and may vary from subject to subject and also from vessel to vessel within a given subject. Pressure less than normal can be noted during techniques used to perfuse an organ, and especially on the collection side of the organ where the removal of fluid from a vein can lead to lower than normal intravascular pressure.

It may be desirable to support vessels in a number of procedures. One procedure involves simply drawing fluid out of the vessel using a pump during, for example, perfusion of an organ. Perfusion typically involves the use of one or more pumps to transport fluid into an organ, and to draw fluid away from the organ. The perfusate may or may not be returned to the organ. Under typical perfusion conditions, the rate at which fluid is drawn out of the vessel may need to be sufficiently high such that the vessel walls cannot maintain patency and subsequently collapse. The cause of vessel collapse may be due to a combination of high flow rates and low pressure on the collection side of the organ. The vessel may collapse either partially, where the vessel wall deforms in such a way that flow into a collection catheter is impeded, or the vessel may collapse completely where flow into the catheter is prevented entirely.

Vessel collapse is particularly prevalent in flaccid vessels such as veins. A particularly problematic case is where the coronary sinus is used to collect fluid perfusing through the coronary circulation of the heart. The coronary sinus can be difficult to deal with when collecting fluid using a collection lumen located within the sinus. This is in part due to the fact that the coronary sinus wall is flaccid and prone to collapse when contacted by a collection catheter tip. This problem is intensified as a result of the low pressures which are generated at the catheter tip as fluid is drawn out of the sinus and these low pressures, in combination with inadequate flow into the sinus, can cause the vessel wall to collapse.

Further, because of the curvature of the coronary sinus, there is a natural tendency for a catheter tip approaching from the right atrium to contact the sinus wall, thus increasing the risk of collapse and damage to the sinus wall e.g. by perforation. Collapse of the coronary sinus can cause venous pooling in the coronary veins and may therefore be fatal. Use of a support device to maintain patency of the coronary sinus and distance the catheter tip from the vessel walls, in accordance with some embodiments of the present invention, minimizes the risk of these complications eventuating. Other veins of the body may also assume a curved course thereby increasing the likelihood of catheter contact and obstruction during collection of blood or perfusate.

The inventive device and methods, in their various embodiments, at least partly overcome the problems referred to above by providing an expandable member which is percutaneously deliverable and is adapted to expand when located inside a target vessel, thereby preventing the vessel from collapsing and thereby maintaining patency. A further advantage of the support device is provided where the support device maintains the catheter tip through which the fluid is drawn or delivered substantially centrally of the vessel, or at least maintains the tip at a distance from the vessel wall. This prevents the tip from aspirating into the vessel wall and occluding the lumen. Further, the support device may act as an anchor when in contact with the vessel wall, limiting movement of the catheter as fluid is collected or delivered.

Perfusion methods incorporate one or more pumps to deliver fluid into or collect fluid from an organ. In one embodiment of the device where the device includes a collection catheter component, and the collection catheter component is attached to a pump, the pressure around the intake of the pump is equal to or less than about −90 mmHg. In some cases, pressures this low will lead to collapse of a vessel wall. Vessel collapse becomes more likely when the pressure at the pump is equal to or less than about −100 mmHg to −115 mmHg, or lower.

Where a pump exerts a very large negative pressure on a perfusion line, cavitation may occur. Under this situation, perfusion must be halted, and the low pressures in the line returned closer to normal. Applicant has found that cavitation is a substantial difficulty in the perfusion of organs, and have found that inclusion of a support device can negate this problem. Accordingly, in another embodiment of the device, where the device includes a collection catheter component, and the collection catheter component is attached to a pump, the device is capable of preventing or delaying cavitation in the collection catheter component, or the pump, or a line connecting the collection catheter to the pump. While cavitation may not be completely prevented it may be at least delayed such that the problem does not occur until a higher flow rate or lower pressure is reached. The presence of the means for supporting the vessel will at least provide that a higher flow rate is necessary to trigger cavitation as compared with the situation where no means for support is present.

In another embodiment of the invention the means for supporting the vessel is capable of maintaining patency of the vessel under conditions of high fluid flow rate in the vessel. In one form of the invention, the fluid flow rate in the vessel is equal to or greater than a value selected from the group consisting of about 20 mL per minute, 160 mL per minute, 180 mL per minute, 200 mL per minute, and 220 mL per minute.

Typically, the fluid flow rate substantially matches the rate of flow of fluid into the vessel from an anatomical region or organ. By maintaining this balance, the organ, anatomical region and their associated vessels will have less chance of damage due to the build up of excess fluid or desiccation.

The support device may be deployed in a vessel associated with a number of different organs or anatomical regions of the subject's body including but not limited to the heart, lungs, brain, liver, kidney, pancreas, intestine, mesenteric system, the upper and lower limbs, thorax, pelvic region and the like. While the present invention is proposed to be used primarily for intravascular applications, it is to be understood that use of the device in non-vascular applications is also possible. For example, the support device may be deployed in any vessel of the body capable of carrying a fluid and prone to collapse such as a lymph vessel, ureter or urethra, bile duct, pancreatic duct, fallopian tube, intestine, oesophagus, or a spermatic duct.

Preferably, the device is adapted to support the vessel during collection of substantially all fluid entering the vessel from an organ or region during a fluid collection procedure. To assist in this regard, occluding means such as an occluding balloon may be utilized to prevent flow from the vessel to other organs or regions. This enables the collection catheter to collect substantially all of the flow entering the vessel. The collection catheter may extend through the occluding balloon although other arrangements may be contemplated. Preferably, the expandable member is adapted to support the vessel during collection of fluid at a rate which substantially matches a rate of fluid flow into the vessel from a region or organ.

The expandable member may also be adapted for use with a delivery catheter during delivery of fluid to a vessel in which there is a propensity for the delivery catheter to move, for example, into branched tributaries of the vessel. Such vessels may include arteries, particularly smaller arteries, or vessels in which there is turbulent blood flow.

The support device may also include an atraumatic guiding tip adapted to make atraumatic contact with the vessel wall when guiding the expandable member into position within the target vessel. Thus, as the expandable member is positioned within the vessel, perforation, bruising, laceration or other trauma is substantially avoided upon contact between the atraumatic tip and the vessel. Once positioned within the vessel, the expandable member can be released from a delivery catheter or sheath and expanded. The atraumatic tip may be curved or shaped to substantially avoid trauma to the vessel wall. Thus, the atraumatic tip may include a "J-shaped" portion, a pigtail portion, a loop portion or a substantially straight portion with a flexible end adapted for atraumatic contact with the vessel wall. The atraumatic tip may also have a smooth surface to encourage deflecting or sliding along the vessel wall. A lubricious or low coefficient of friction coating may be utilized to encourage deflection or sliding.

In one embodiment, the expandable member of the support device is a radially expanding member. Radial expansion may be achieved using any suitable means. In one preferred form, the expandable member includes a framework formed from a material having super-elastic and/or shape memory properties, enabling the device to self-expand to a particular shape when released from a delivery catheter. In other forms, the expandable member may include a framework which is designed to be controllably expanded e.g. by mechanical means, when positioned within the vessel.

Preferably, the support device includes a radiopaque or other marker for use with an imaging system known in the art for positioning the device within the blood vessel. The marker may be incorporated into the atraumatic tip. Alternatively, there may be one or more marker regions incorporated into the expandable member itself. In another embodiment, markers are incorporated into the atraumatic tip and the expandable member.

The expandable member may be coupled to a stem or shaft (such as a guidewire) for delivery of the expandable member to a deployment site within the vessel. In one embodiment, the distal end of the expandable member may be movably coupled to the stem, whereas the proximal end of the member is fixedly coupled to the stem. In this arrangement, the distal end of the member slides along the guidewire enabling the member to expand and collapse. This configuration may alternatively be provided in the reverse, where the distal end of the expandable member is fixedly coupled to the guidewire with the proximal end movably coupled to the guidewire, although additional modification may be required to facilitate recapture of the expandable member for removal from the vessel.

In a further embodiment, the expandable member is integral with the stem. Thus, a distal region of the stem provides a plurality of pre-shaped segments or struts, adapted together to form an expandable member under certain conditions. For example, when released from a delivery catheter into the target vessel. Preferably, the pre-shaped segments or struts are filamentous and composed of a substantially superelastic, shape memory or other material which may be subjected to deformation (for collapsed delivery to the target site) and recover to an expanded condition when released from a catheter.

In another embodiment, the expandable member includes one or more loop portions with each of the loop portions attached at a first loop end to a distal end of a lumen, and at a second loop end to a control stem extending through the lumen. The one or more loop portions have a collapsed condition in which they are substantially within the delivery lumen, and are controllably expandable by advancing the control stem to eject one or more of the loops therefrom. An atraumatic guiding tip may be incorporated into one or more of the loop portions. Alternatively, a separate atraumatic tip may be provided in communication with the control stem.

The expandable member may have 2, 3, 4, 5, 6 or more loop portions. Determination of the number of loop portions may be based on the size of the vessel being supported, and/or the stiffness of the vessel, where more loop portions may be required to support a vessel having particularly flaccid walls. The support device may also include retention means to retain the expandable member in an expanded condition. Retention means may include, for example, an outer stem on the support device. The proximal end of the outer stem may be fastened to an anchor point outside the subject's body to prevent collapse of the expanded member during collection of fluid from the vessel, especially where very low pressures are generated.

The atraumatic tip may be provided at any suitable distance from the distal end of the expandable member, as may be necessitated by the anatomy of the vessel being supported. For example, the atraumatic tip may be provided 0.25 to 5 centimeters from a distal end of the expandable member when it used in the coronary sinus. However, it is to be understood that these values are examples only and that the atraumatic tip may be provided at any suitable distance from the expandable member, as may be influenced by the size and shape of the target vessel and the surrounding structures.

Preferably, the atraumatic tip is made from, includes or is coated with a lubricious material or a material having a low coefficient of friction to encourage the tip to "slide" off the vessel wall on making contact. Some suitable materials which may be considered to have sufficiently low coefficient of friction properties may include but are not limited to biocompatible high density polyethylene (HDPE), Teflon®, polypropylene, polyethylene, Microglide™, low friction chromium and silicon In a further embodiment of the invention there is provided a device including: a plurality of support members disposed in an array having an expanded state and a collapsed state, wherein in the collapsed state, the array is sized for delivery to the vessel through a lumen of a catheter, and wherein in the expanded state, the array is sized to be greater than an internal dimension of the catheter, wherein the support members are biased to the expanded state. In one embodiment of the device, in the expanded state, the support members are substantially parallel to a longitudinal axis of the catheter.

Embodiments of the present invention may be used to support a range of blood vessels servicing different organs of the body including the heart, lung, liver, kidney, brain, intestine, testicle, ovary, spleen, stomach, prostate and pancreas. The present invention may also be used to support blood vessels servicing an entire anatomical region such as a limb, the pelvis, the chest, the breast and the mesenteric system. The skilled person will possess sufficient knowledge to decide the appropriate vessel or vessels to target according to which organ or anatomical region is to be catheterized.

For example, where the organ is the heart the arterial catheter may be placed in the coronary artery. A venous catheter may be placed in the coronary vein, typically in the coronary sinus. Where the organ is the liver, an arterial catheter may be placed in the hepatic artery and a venous catheter may be placed in the hepatic vein. This may be performed with a reduction of flow in the portal vein utilizing acute administration of, for example, Octreotide or Terlipressin.

Where the organ is the brain, arterial catheters may be placed in the left and right vertebral arteries, and also the left and right internal carotid arteries. Venous catheters may be placed in the left and right internal jugular veins.

Perfusion of the kidney may be performed by locating an arterial catheter in the renal artery. A venous catheter may be placed in the renal vein. Where the organ is the stomach, an arterial catheter may be placed in the gastric artery. A venous catheter may be placed in the portal vein or the hepatic veins.

Perfusion of the spleen may be achieved by placing an arterial catheter may in the splenic artery, and a venous catheter in the splenic vein, the portal vein, or the hepatic veins. To perfuse the intestines, an arterial catheter may be placed in the superior and/or inferior mesenteric artery. A venous catheter may be placed in the portal vein or hepatic veins.

Where the anatomical region is the pelvis, an arterial catheter may be placed in the internal iliac artery. Where the organ is a testicle or an ovary, an arterial catheter may be placed in the right or left testicular or ovarian artery. A venous catheter may be placed in the right or left testicular or ovarian vein. To perfuse the prostate, an arterial catheter may be placed in the inferior vesicle artery or the internal iliac artery. A venous catheter may be placed in the inferior vesical vein or the internal iliac vein.

Where the organ is a lung, an arterial catheter may be placed in the pulmonary artery. A venous catheter may be placed in one or both pulmonary veins. In one embodiment, selective delivery can be provided to one lung only, or only one lobe of a lung. Thus, the arterial catheter may be located in the relevant branch of the pulmonary artery and the venous catheter would be located in the relevant (i.e. upper or lower) pulmonary vein, depending on the lobe being treated. To perfuse the breast, an arterial catheter may be placed in the internal mammary artery and the intercostal arteries. A venous catheter may be placed in the intercostal veins.

The devices described herein are proposed to be useful in delivering and/or collecting fluids from organs and anatomical regions of the body. Accordingly, in a further aspect the present invention provides a method for percutaneous delivery and/or collection of a fluid to or from an organ or an anatomical region of a subject, the method including the step of supporting a vessel of the organ or the anatomical region. The vessel is maintained substantially patent during delivery or collection of fluid to or from the organ or anatomical region, especially where the fluid pressure in the vessel is less than the minimum pressure normally found in the vessel. Under normal perfusion conditions, and where the fluid pressure in a vessel decreases to a sub-normal level, vessel wall collapse may ensue leading in turn to cavitation in perfusion lines. In one embodiment of the method, cavitation in the collection catheter component, or the pump, or a line connecting the collection catheter to the pump is substantially prevented or delayed.

The method may include the step of placing a collection catheter in the vessel and attaching a pump to the collection catheter. While any suitable pump may be used, typically a peristaltic pump is used. The collection catheter may be placed in an outflow vessel of the organ or anatomical region. The method may also include the step of placing a delivery catheter in an inflow vessel of the organ or anatomical region, for example where it is desired to introduce a fluid into the organ or anatomical region or to recirculate a fluid through the organ or anatomical region. Again, a pump is typically attached to the delivery catheter to assist delivery of the fluid into the subject organ or anatomical region.

In another form of the method the collection catheter collects fluid from the target region at the outflow vessel such that the collected fluid is substantially prevented from entering the general circulation. A higher level of isolation is provided whereby the method further includes the step of substantially occluding flow from the outflow vessel to the general circulation. The occlusion step allows the collection catheter to collect substantially all flow entering the vessel. In one form of the method the step of occluding is performed by inflating an occluding balloon around the collection catheter placed in the outflow vessel. Optionally, an occluding flange is placed around the collection catheter.

As discussed infra the present invention allows for perfusion at flow rates that would normally lead to collapse of vessels associated with the organ being perfused, or cavitation occurs in the perfusion circuit. Accordingly, one form of the method includes the use of high fluid flow rate in the vessel. The fluid flow rate in the vessel may be equal to or greater than a value selected from the group consisting of about 20 mL per minute, 160 mL per minute, 180 mL per minute, 200 mL per minute, and 220 mL per minute.

In some situations it may be desired to recirculate a fluid through an organ or anatomical region of a subject. Accordingly, one embodiment of the method further includes the step of connecting a re-perfusion circuit between the delivery and collection catheters and recirculating the collected fluid. If fluid is lost in the course of reperfusion then the method may include the further step of adding a replenishing fluid to the re-perfusion circuit. Where recirculation is implemented the method may include the further step of oxygenating blood collected from the inflow vessel prior to re-perfusing it into the organ or anatomical region.

It is to be understood that while embodiments of the present invention have been described in the context of anterograde circulation and perfusion, it will be apparent that the methods may also be suitable for retrograde perfusion of an organ or an anatomical region. Typically, for anterograde perfusion the inflow vessel is an artery, and the outflow vessel is a vein. Where retrograde perfusion is desired the inflow vessel is a vein, and the outflow vessel is an artery.

The present methods may be used in respect of any organ or anatomical region where support of an associated vessel is necessary or desirable due to a propensity for collapse of the vessel. Exemplary organs include the heart, lung, liver, kidney, brain, intestine, testicle, ovary, spleen, stomach, prostate, and pancreas. The anatomical region may be a limb, the pelvis, the chest, the breast or the mesenteric system.

The vein may be any vein of the body requiring support including, but not limited to a coronary vein (including the coronary sinus), a left or right internal jugular vein, a hepatic vein, a renal vein, a cephalic vein, an inferior vesical vein, a pulmonary vein, an internal iliac vein, a portal vein, a splenic vein, a femoral vein, a saphenous vein, a subclavian vein, an intercostal vein, an axillary vessel, a left or right testicular vein, a left or right ovarian vein, a pulmonary vein or tributaries thereof.

The artery may be any artery of the body requiring support including, but not limited to a coronary artery, a left or right vertebral artery, a left or right internal carotid artery, an inferior vesicle artery, an internal iliac artery, a renal artery, a gastric artery, a splenic artery, a superior or inferior mesenteric artery, an internal iliac artery, an internal mammary artery, an intercostal artery, a right or left testicular artery, a left or right ovarian artery, a pulmonary artery or tributaries thereof.

The method may further include the step of using an imaging technique to position the delivery catheter and/or collection catheter in the inflow and outflow vessels of the target region, the imaging technique including one or more of deployment of radiographic contrast, deployment of nuclear medical probes, deployment of in vivo probes sensitive to oxygen, hydrogen, pH or the like and deployment of labelled micro- or nano-particles.

It is proposed that the devices described herein are useful in the percutaneous delivery and/or collection of therapeutic and diagnostic agents to a discrete tissue of the body. Accordingly, a further aspect of the invention provides a method for percutaneous delivery and/or removal of a therapeutic or diagnostic agent to a target organ or anatomical region of a subject, the method including the step of supporting an inflow or an outflow vessel. In one embodiment the method includes the use of a percutaneously deliverable device as described herein. The therapeutic agent may be, or may be carried by the fluid referred to herein. Examples of therapeutic agents deliverable in the context of the present methods and devices includes a chemotherapy pharmaceutical, an antibiotic, a vasodilator, a vasoconstrictor, a peptide, a hormone, a stem cell, a cytokine, an enzyme, a gene therapy agent, a polynucleotide, blood, and serum.

An advantage of the present devices and methods is that it is possible to substantially isolate the circulation of an organ or anatomical region and administer (and optionally recirculate) a therapeutic agent. By collecting substantially all therapeutic agent leaving the outflow vessel, it is possible to prevent exposure of the systemic circulation to the agent. This is of significant advantage where the agent is toxic (such as a chemotherapeutic agent), or where it is otherwise undersirable to expose other tissues (for example a gene therapy agent). Similarly, where the agent is only available in limited quantities, administering the agent to only the target tissue is clearly desirable. It follows that since a smaller quantity of the therapeutic agent is used in a highly localized manner, the present invention provides a cost reduction for the therapy.

For treatment of organs and anatomical regions the inventive methods and devices may be used to deliver a therapeutic or diagnostic agent such as a small molecule, a gene or a cell for the treatment of conditions including but not limited to diabetic nephropathy, renal fibrosis, glomerulonephritis, contrast-induced nephropathy, and renal transplant rejection, renal cancer (for the kidney); emphysema, cystic fibrosis, pulmonary fibrosis, pneumonia, lung malignancy and pulmonary hypertension, pulmonary embolism (for the lungs); neurodegenerative diseases such as Alzheimer's disease, Parkinson's disease and Huntington's disease, cerebral ischemia, epilepsy and brain tumor (for the brain); viral hepatitis, autoimmune hepatitis, cirrhosis, hepatocellular carcinoma, hepatic metastasis, and fatty liver (for the liver); myocardial infarction, angina, coronary heart disease, congestive heart failure, myocarditis and ventricular hypertrophy (for the heart); diabetes and pancreatic cancer (for the pancreas); deep vein thrombosis, limb ischemia (for limb); inflammatory bowel disease and bowel cancer (for the intestines).

IN THE FIGURES

The present invention will now be described in greater detail with reference to the accompanying drawings. It is to be understood that the particularity of the accompanying drawings does not supersede the generality of the preceding description of the invention.

FIGS. 1a to 1c illustrate a support device according to an embodiment of the present invention. FIG. 1a shows the expandable member in an expanded condition. FIG. 1b shows the expandable member in a collapsed condition within a catheter for delivery to a vessel. FIG. 1c shows the expandable member after deployment from the catheter into the vessel.

DETAILED DESCRIPTION OF THE INVENTION

Figure 1A:
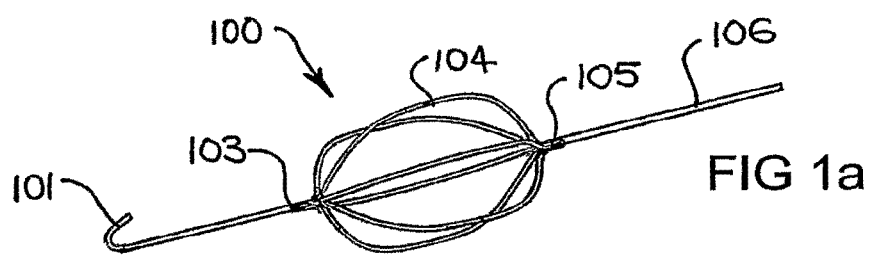

While the support device of the present invention may be used in a range of different vessels, including blood vessels, it has particular application in procedures where an organ or anatomical region is undergoing localized perfusion with a therapeutic, diagnostic or other agent. For simplicity, these agents will be hereinafter referred to as therapeutic agents. However, it is to be understood that the term "therapeutic" is not to be construed as limiting, and that it includes, without limitation, therapeutic, diagnostic, prophylactic and other agents not specifically identified herein, but which would be considered by the relevant skilled addressee to be suitable for perfusion to an organ or anatomical region.

Perfusion may be total perfusion, where the entire organ is totally or substantially isolated from the systemic flow, or partial perfusion where only a portion of the organ is substantially isolated. Localized perfusion of this kind presents advantages by improving efficacy and the time exposure of the therapeutic agent to the relevant cells. It also limits exposure and hence toxicity to non-target cells as described in brief above. However, it is to be understood that the present invention may also be used simply to collect or drain fluid from an organ or region. Collected fluid may be removed from the subject and re-circulated into the organ, filtered and/or treated, or discarded.

In some organs, it may be difficult to achieve total isolation, so partial isolation and perfusion may be performed, for example to the right or left lobe of the liver. Despite partial perfusion being capable of delivering therapeutic agent to merely a part of the organ, significant therapeutic benefit may still be achieved.

Particular benefit may be achieved where perfusate is collected after perfusing the target organ, so as to prevent subsequent circulation of the therapeutic agent to other regions of the body where toxic effects may be observed, or the therapeutic agent wasted. The benefit may be improved further where collected perfusate is re-circulated into the target organ utilizing any therapeutic agent which remains after a first pass through the target organ. This may be achieved using the approach described in published patent application WO2005/082440, the entire contents of which are herein incorporated by reference.

As discussed infra, when fluid is collected from vessels draining from a target organ or region, one or more of these vessels may require cannulation with a collection catheter. When fluid is drained through these collection catheters, the vessels in which they are positioned become susceptible to collapse as the pressure inside decreases. While some vessels may be more susceptible to collapse than others, the support device of the present invention can provide advantages by supporting and stabilizing the vessel and even anchoring the collection catheter in position. The support device of the present invention may facilitate or at least improve the performance of perfusion. In some instances, the advantages of the present invention have been found to be essential to maintaining adequate positioning of collection catheters and flow rates within the vessel during perfusion.

The right and left lobes of the liver have been identified as possible target regions and in this context, the support device may be deployed in one of the hepatic veins to support and maintain patency of the vein as fluid (e.g. perfusate) is collected from the liver. However, it is to be understood that fluid from many other organs or regions may be accessed in this way.

Deploying the support device may also protect the vessel wall by maintaining the tip of the catheter substantially centrally of the vessel or at least at a distance from the vessel walls to prevent aspiration or cavitation. Deployment of the device may refer to partial or complete deployment. In complete deployment, the entire expandable member is released from the catheter and expanded to its full extent. In partial deployment, part of the expandable member is retained within the catheter and the amount of expansion is limited by the diameter of the catheter opening. Partial deployment may be useful where, for example, during deployment it is found that the diameter of the expandable member may exceed the vessel diameter by an unsafe amount and complete deployment is likely to damage the vessel wall. Limiting expansion of the device by partial deployment may avoid vessel damage.

Partial deployment may also stabilize the expandable member by limiting its movement relative to the catheter tip. Thus by retaining part of the expandable member within the catheter, torsional, axial and lateral movement of the member, relative to the catheter is prevented or at least minimized by the struts of the expandable member being in abutment with the internal surface of the catheter. Alternatively, the expandable member may be modified at the proximal end, for example by incorporating a lead, a link or other means to limit the extent of movement possible between the catheter tip and the expandable member once deployed. As a further positioning aid, markings may be provided at the proximal end of the control stem/shaft, outside the patient's body. As the device is released into the vessel, the markings may be utilized to indicate the distance of device deployment, past the catheter tip.

During collection of fluid from the vessel, low pressures may develop at the collection device tip, particularly where a roller/peristaltic pump or the like is used to draw fluid from the target organ out of the vessel. This may be indicated by pressures in a lumen feeding into the pump as low as, for example, −190 mmHg, although clearly these pressures are variable depending on the vessel type, health and age of the subject, characteristics of the perfusion circuit and the like. In the absence of the inventive support device, these pressures can cause the vessel to collapse. Not only would vessel collapse affect the perfusion procedure, vessel collapse can also cause venous pooling in the organ and irreversible tissue damage.

The advantages and benefits of the present invention will be expanded upon in the following detailed description presenting some of the preferred embodiments of the invention, and the specific Examples which follow. It is to be understood that the embodiments and examples provided herein are intended to indicate how the present invention may be performed and are not intended to be limiting on the scope of protection sought as is defined in the claims appended hereto.

Figure 1B:
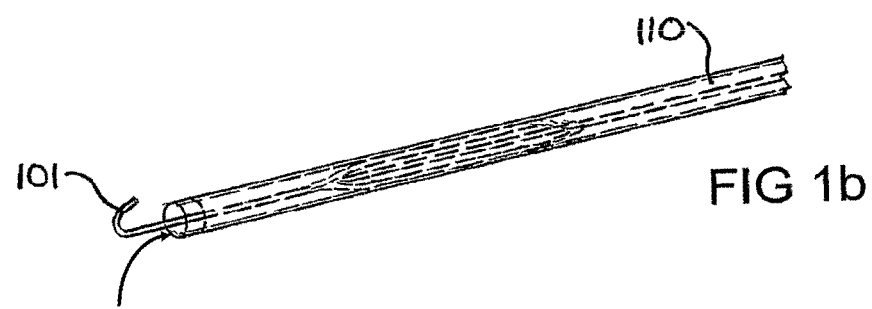
Figure 1C:
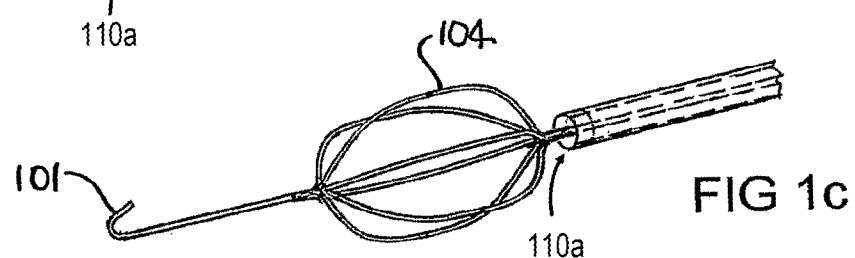

FIG. 1a shows an example of an expandable member, in its expanded condition, suitable for supporting a vessel. Expandable member 104 is provided in the form of an expandable framework and is adapted to be percutaneously deliverable to the blood vessel in a collapsed condition. FIG. 1b shows the expandable member in a collapsed condition within a catheter 110, in which ends 105, 103 have been drawn apart to radially reduce the member. When collapsed within catheter 110, atraumatic tip 101 may protrude from a collection opening 110a of the catheter to assist in guiding the support device into the vessel prior to deployment. When the expandable member has been guided into the target blood vessel, the catheter 110 is retracted (or the expandable member is pushed out of the catheter), deploying the device into the vessel where it expands. FIG. 1c shows the support device fully deployed from the collection opening 110a of the catheter, with the expandable member in its fully expanded condition.

A guidewire or stem 106 extends within the catheter 110 and is used to deliver the device from a point of entry through the peripheral vasculature to the target vessel. Atraumatic tip 101 coupled to the expandable member 104, is adapted to make atraumatic contact with vessel walls during placement of the device by deforming or deflecting off the vessel wall on contact. This can be achieved by incorporating flexibility into the tip so that it deforms upon contact with the vessel wall. Alternatively or additionally, the tip may be shaped or curved to avoid trauma.

The atraumatic tip may take any one of a number of forms. In the examples illustrated in FIGS. 1 to 3, the atraumatic tip 101, 201 is J-shaped. However, other shapes are considered to be suitable, including but not limited to those illustrated in FIG. 4. For example, the atraumatic tip may have a cross section which is enlarged relative to the guidewire radius, and have a smooth surface so as to avoid causing perforation when the tip comes into contact with the vessel wall. One such example is shown in FIG. 4a where the atraumatic tip 401 is tear-shaped. Alternatively, the atraumatic tip may include a portion having a pigtail shaped curve 402 (FIG. 4b), or an angled tip (not shown).

Preferably, the expandable member is formed from a biocompatible superelastic material, or alternatively from a shape memory material or a material which exhibits both of these properties, being capable of recovery after deformation for delivery in a collapsed or compressed state within a catheter. Devices manufactured using these materials can be collapsed for percutaneous delivery to a deployment site and then resume a known shape on deployment. A range of biocompatible materials may be suitable such as alloys of nickel and titanium (e.g. Nitinol). Other suitable biocompatible materials include but are not limited to polymers and plastics such as hydrophilic plastics, ceramics and the like.

Figure 3:
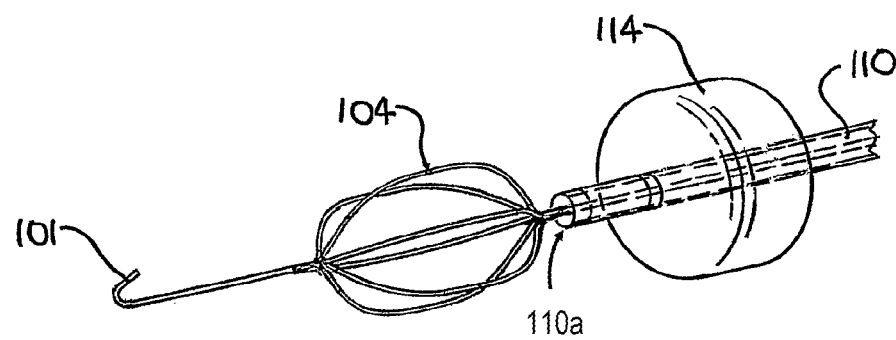
FIG. 3 illustrates the support device of FIGS. 1a to 1c, in the expanded configuration, with the addition of an occluding balloon, inflated around the catheter.
Figure 4A:
FIGS. 4a and 4b illustrate variations of an atraumatic guiding tip for use with embodiments of the present invention.
Figure 4B:

FIG. 3 illustrates the support device of FIGS. 1a to 1c, with an occluding balloon inflated around catheter 110. The occluding balloon 114 may be utilized during collection of fluid from an organ or region of the body in isolation, where substantially all of the fluid flowing out of the organ or region is collected by the catheter 110. The occluding means substantially prevents blood, therapeutic agent and/or other fluids entering the vessel from flowing on to other organs or regions, and permits collection of substantially all of the fluid entering the vessel. Collected fluid may then be analyzed and/or re-oxygenated and/or perfused through the organ, discarded or handled otherwise. The occlusion means may include an occluding balloon, flange, disc or other means.

Catheter 110 is delivered to the vessel with the balloon 114 in a deflated condition. The expandable member is delivered, through the collection opening 110a of the catheter, and deployed inside the vessel. The balloon is then inflated around the catheter and substantially all the fluid in the vessel flows through the catheter and into a perfusion set or reservoir to which it is connected.

A pump, syringe or other means may be incorporated into the perfusion set to draw fluid out of the vessel, through the collection opening 110a of the catheter, at a rate which substantially maintains the required flow through the organ or region, or through a re-perfusion circuit. As fluid is drawn out of the vessel through the catheter, the expanded support structure supports the vessel walls, preventing collapse or cavitation which might otherwise result from the low pressures or high flow rates generated at the catheter tip, maintaining patency and ensuring flow in the circuit. The expandable member may also anchor the device in position within the vessel, substantially precluding movement of the device and ensuring that the catheter is retained in an optimal location for collection of fluid.

Figure 8A:
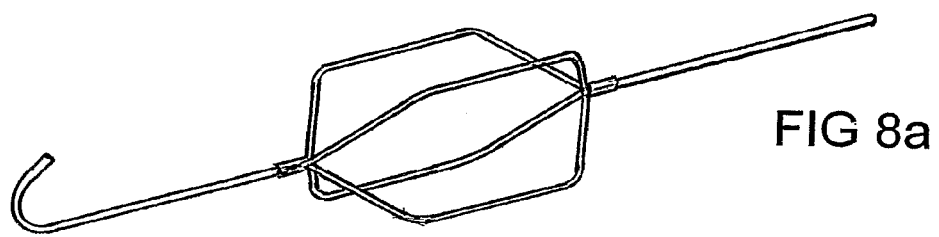
FIGS. 8a to 8c illustrate various expandable members having different geometric designs.
Figure 8B:
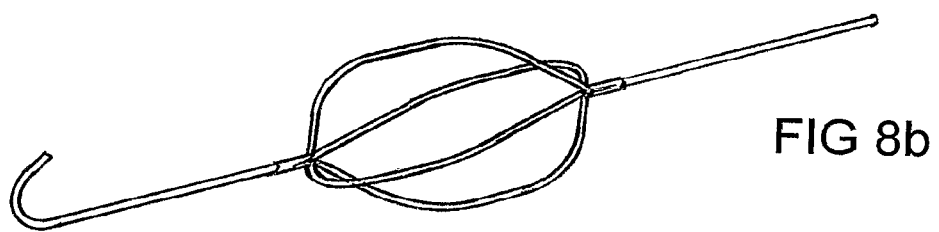
Figure 8C:
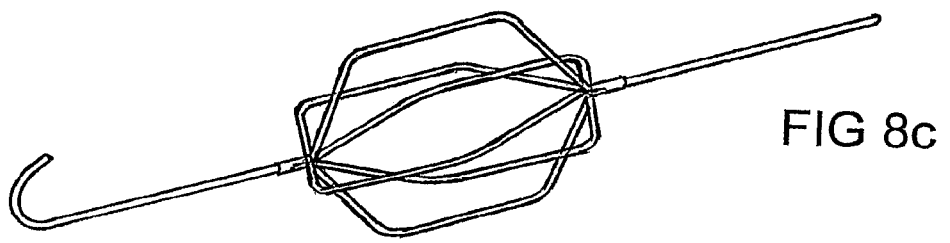

The expandable member may take a range of different shapes when in an expanded (or collapsed) configuration, and may provide any number of supporting filaments or struts. The design of the expandable member may be based on a range of criteria including but not limited to the size and strength of the vessel wall and the flow rates and pressures likely to be generated near the device. Some of these embodiments are illustrated in FIGS. 8a to 8c although these are examples only and are not intended to limit the scope of the invention as broadly described herein. FIGS. 8a to 8c illustrate expandable members having elongate portions in the supporting struts adapted for contact with the vessel wall. In the example in FIG. 8b, the supporting struts are slightly rounded to reduce trauma to the vessel walls. FIG. 8c provides additional struts when compared with FIG. 8a, as may be necessitated in particularly flaccid vessels requiring more substantial support.

Embodiments illustrated herein provide expandable members with a substantially elongate structure adapted for coaxial insertion into and placement within the vessel. The elongate structure supports the vessel over a length on the elongate portions of the struts substantially parallel to and in contact with the vessel wall. These elongate portions may be substantially straight, or may be curved (e.g. FIG. 8b). Supporting the vessel wall over a length of the support device, compared with the point of supports of the prior art, improves the capacity of the device to maintain patency, even when very low pressures and high flow rates are generated at the catheter tip, and also reduces the likelihood of the device causing damage to the vessel wall.

The elongate portions may have a length which is about the same as or greater than the diameter of the vessel being supported, or some multiple of the vessel diameter, or for example from 1 mm up to 30 mm depending on the vessel size and structure. The length of the elongate portion may be selected according to the vessel being supported, the size of the catheter being used and the flow rates and pressures likely to be generated at the catheter tip.

Preferably, the elongate portions of the expandable member which contact the vessel wall, are just adjacent the distal tip of the catheter when the device is fully deployed. Thus, a proximal end of one or more of the elongate portions may commence, for example, within 0.1 to 25 mm of the catheter tip, or at least at a distance which is less than the diameter of the catheter opening. This prevents the vessel wall from being drawn into the space between the catheter tip and the start of the elongate portion of the expandable member which contacts the vessel wall.

Further, the device may be configured so that when it is in an expanded condition, the distance between adjacent elongate portions is sufficiently small to prevent the vessel wall from being drawn into gaps between them. For example, the distance between adjacent elongate portions may be less than the diameter of the catheter. Alternatively, the distance between the adjacent elongate portions may be less than, for example, 3, 2.5, 2, 1.5, 1 or 0.5 mm, depending on the size and type of the target vessel, and the diameter of the collection catheter being used.

Preferably, the support device possesses sufficient mechanical strength to maintain patency during collection of fluid, withstanding the deformation forces which may occur in response to suction or low pressures produced at the collection catheter tip. In some embodiments however, it may also be desirable for the device to exhibit some flexibility, and conform to the shape of the vessel when deployed. Thus, the support device is capable of providing support and maintaining patency along a length of the vessel, even where there is a curve in the vessel wall.

Figure 2:
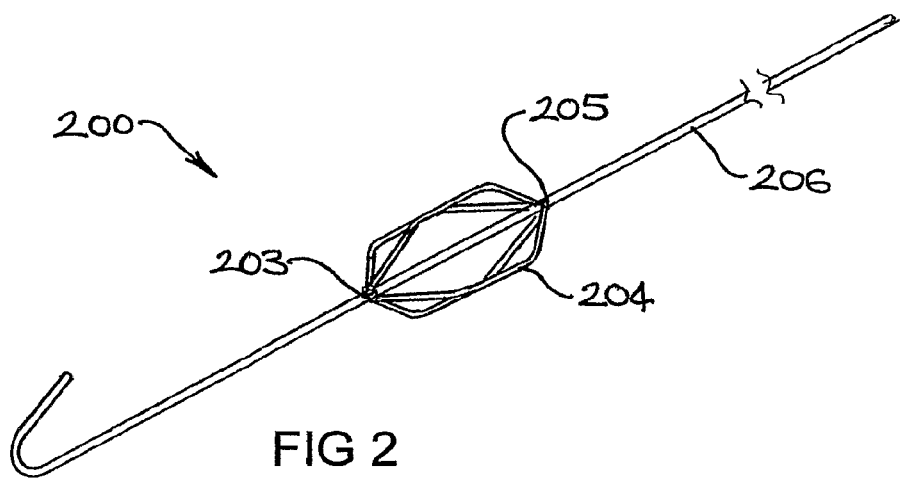
FIG. 2 illustrates a support device according to another embodiment of the present invention, where the expandable member is in communication with a stem or shaft such as a guidewire.

An alternative embodiment of a support device 200 is illustrated in FIG. 2. Proximal end 205 of the expandable member 204 is fixedly attached to a stem or shaft 206, whereas distal end 203 of the expandable member is movable and able to slide over part of the shaft. This enables the member to collapse radially for delivery inside a delivery catheter, and also facilitates recapture of the device.

Figure 5:
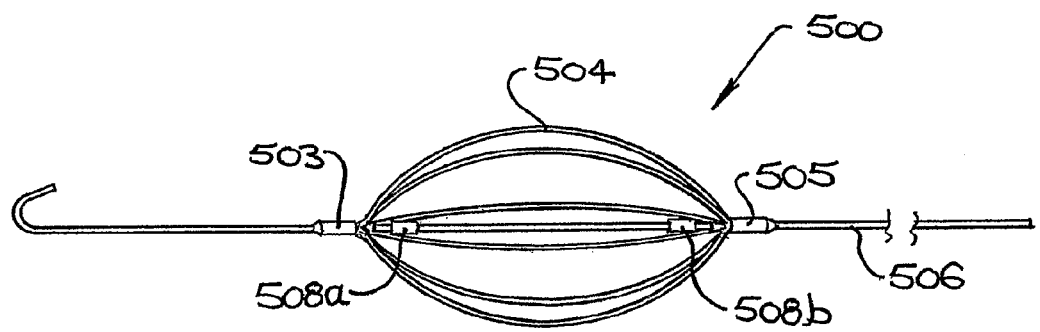
FIG. 5 illustrates a support device according to another embodiment of the invention, incorporating stops to limit movement of the expandable member.

FIG. 5 illustrates another alternative embodiment of a support device shown at 500 in an expanded condition. In this embodiment, both the proximal end 505 and the distal end 503 of the expandable member are movable along a stem or shaft 506 used to deliver the device to the vessel. Stops 508a, 508b are provided at fixed locations on a distal portion of the shaft, arranged between ends 503, 505 of the expandable member. These stops may consist of a small ring, crimp or node of increased diameter, relative to the shaft diameter, and prevent the ends of the expandable member from moving across the stop. This facilitates deployment and retrieval of the expandable member from a catheter.

Figure 10:
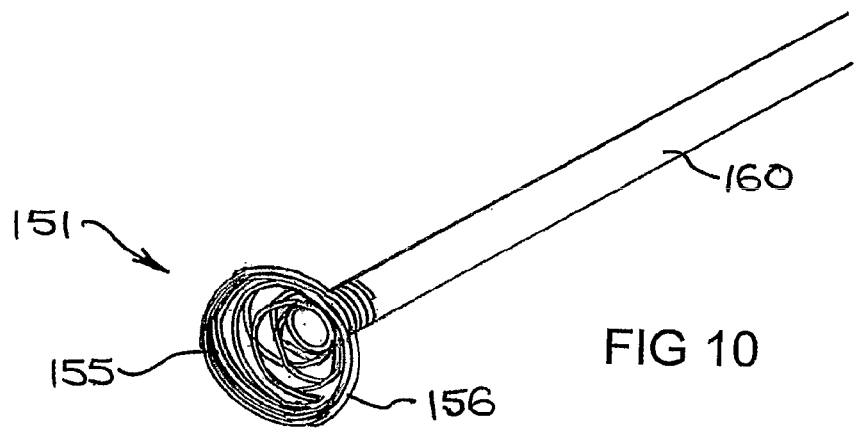
FIG. 10 illustrates an expandable member according to another embodiment of the present invention.

FIG. 10 illustrates a support device 151 consisting of an expandable framework 155 having a woven or braided, basket-like configuration when in the expanded condition. In this arrangement, the support device may also include occluding means in the form of a thin flow-proof coating 156 on the inner and/or outer surface of framework 155 to prevent flow of liquid from the vessel. Thus, substantially all fluid in the vessel may be collected by catheter 160. The flow-proof coating may be made from biocompatible silicon, elastomer or flow-proof polymer.

Preferably, the support device includes a radiopaque or other marker so that it can be positioned within the target vessel using an imaging system such as those generally known in the art. This enables the physician to position and deploy the expandable member into the blood vessel accurately. The marker may be incorporated into the expandable member and/or into an atraumatic guiding tip which may be incorporated into the support device.

Preferably, the atraumatic tip is manufactured from, includes or is coated with a lubricant and/or a material having a low coefficient of friction. Many materials having low coefficient of friction properties may be used including but not limited to biocompatible high density polyethylene (HDPE), Teflon®, polypropylene, polyethylene, Microglide™, low friction chromium and silicon to name a few. This improves the performance of the atraumatic tip, so that it "slides" along the vessel wall upon making contact, thereby substantially avoiding trauma. Use of an atraumatic guiding tip improves the safety and ability to position the expandable member in the target vessel. Moreover, since the atraumatic tip may exhibit greater flexibility than the rest of the device, the device is easier to manipulate into position.

The atraumatic tip may be provided at a distance from the distal end of the expandable member which enables a physician to guide the expandable member into position within the target vessel. This distance may be anywhere from, for example, 0.25 to 5 centimeters from the distal end of the expandable member when in an expanded condition, although it is to be understood that larger or smaller distances may be utilized, depending on the location of the target vessel and the anatomy surrounding it.

Figure 6A:
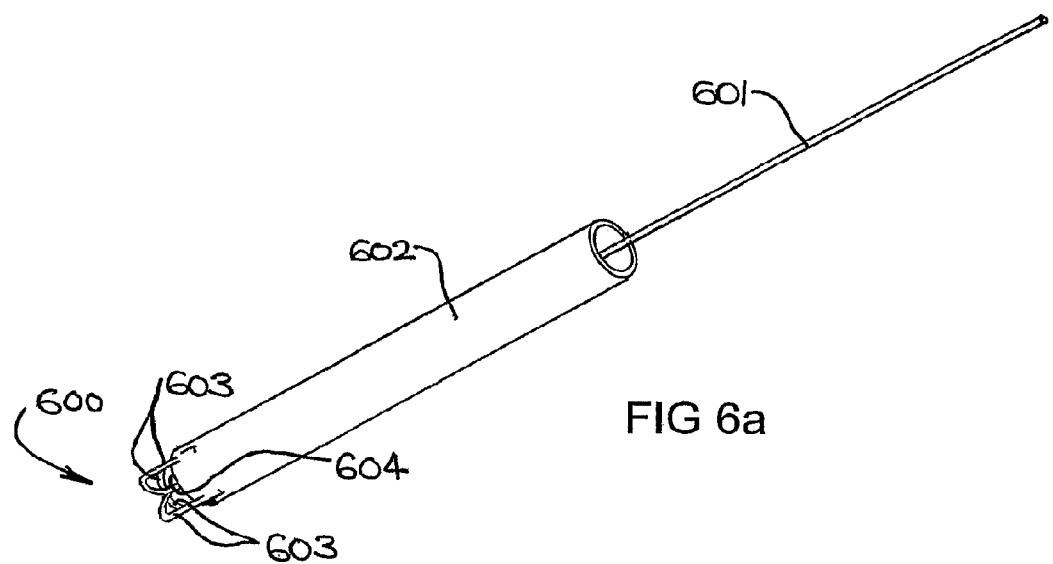
FIGS. 6a and 6b illustrate a support device having 4 expandable loop portions, according to an embodiment of the present invention.
Figure 6B:
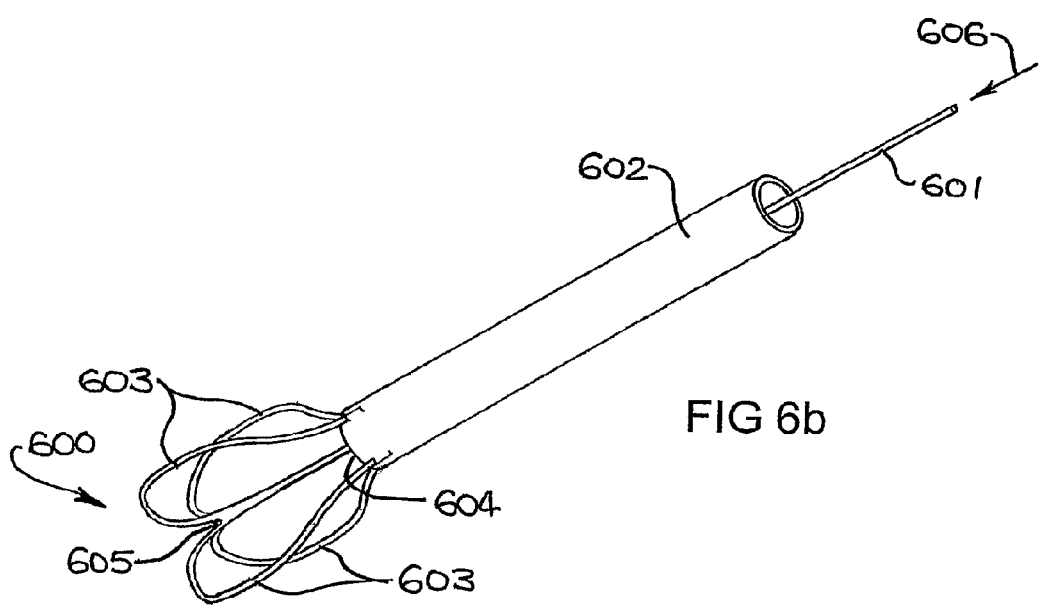

Referring now to FIGS. 6a and 6b, another example of a support device 600 is shown. A lumen 602 has a control stem 601 extending therein. Four loop portions 603 are provided. Each loop portion is attached at a first loop end to a distal end 604 of the lumen, and at a second loop end to the control stem at 605. The loop portions are controllably expandable by advancing the control stem within the lumen in the direction shown by arrow 606 (FIG. 6b). The support device is percutaneously deliverable with the plurality of loop portions housed substantially within the lumen 602 as illustrated in FIG. 6a and expandable as illustrated in FIG. 6b.

Figure 7A:
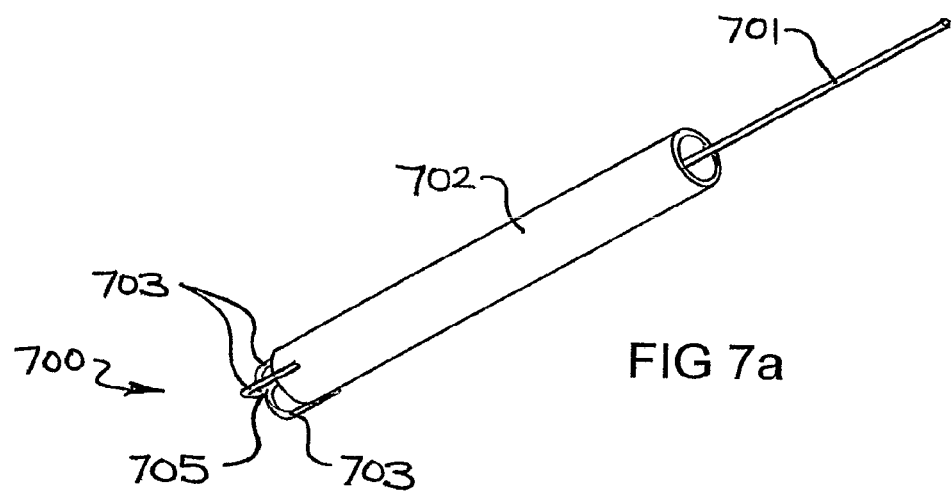
FIGS. 7a and 7b illustrate an alternative support device having 3 expandable loop portions, according to another embodiment of the present invention.
Figure 7B:
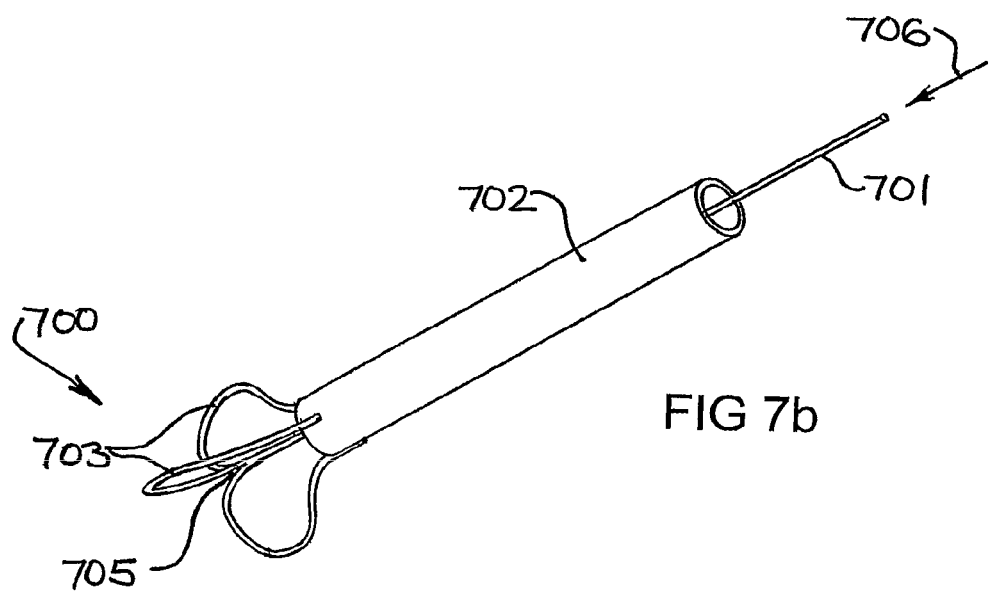

Whilst the embodiment illustrated in FIGS. 6a and 6b provides 4 loop portions, it is to be understood that any number of loop portions may be used. The number of loop portions incorporated into the device may depend on, for example, the anatomy of the vessel being supported, and/or the size of the catheter used to deliver the device. FIGS. 7a and 7b illustrate another example of a support device 700 which provides 3 loop portions 703 attached to control stem 701 at juncture 705. The 3 loop portions are contained during delivery substantially within lumen 702 (FIG. 7a), and are controllably expandable to maintain patency within the blood vessel by advancing control stem 701 in the direction of arrow 706 (FIG. 7b). The rounded edges of the loop portions present a reduced risk of damaging the vessel walls, e.g. by perforation or bruising during delivery.

The one or more loop portions may be attached to or near the distal end of the delivery lumen in any suitable manner. The point of attachment may be inside or outside the lumen. The loops may be manufactured from any suitable material such as a metal, metal alloy, plastic, polymer, or other filamentous material or composite. The one or more loop portions may be attached at a second loop end to the control stem by soldering, fusing, an adhesive, or any other suitable means. In another embodiment, the loop portions may be attached to a first and a second loop end to the control stem.

The support structure of FIGS. 6a, 6b, 7a and 7b may further include an atraumatic guiding tip of the kind described above to aid in positioning the support structure within the blood vessel. Alternatively, parts of the loop portions which may protrude from the lumen when the loop portions are in their collapsed state may be used to guide the support structure into the blood vessel. One or more of the loop portions may be provided with a radiopaque or other marker to assist in this regard.

Retention means may also be provided with the support structure to retain the expandable member in an expanded condition within the vessel. The retention means may be in the form of a clamp, clip, thumb-slide or the like accessible from outside the patient's body, and may facilitate adjustment of a deployed expandable member during a procedure. Retention means may also impart additional rigidity and strength to the expandable member. Thus, the retention member may be used to counteract excessively low pressures which may otherwise cause the expanded member to fail.

Figure 9:
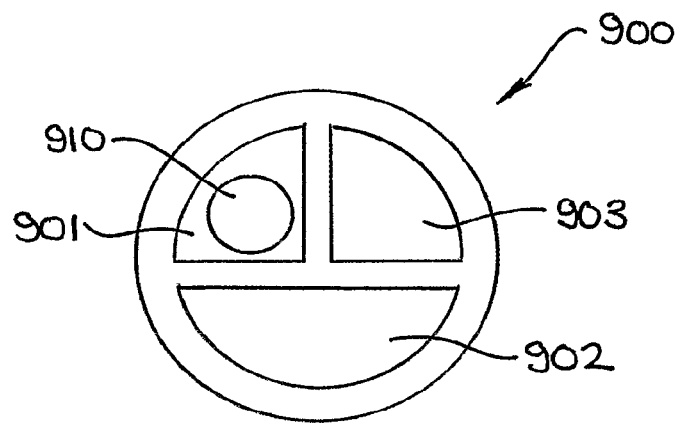
FIG. 9 illustrates a cross section of a catheter for use with embodiments of the present invention.

A support structure of the kind illustrated in the Figures may be delivered within a multilumen catheter 900 of the kind illustrated in cross section in FIG. 9. Using this catheter, the support device 910 can be delivered through a first internal lumen 901 without interfering with flow in a second lumen 902. A third lumen 903 may be provided for monitoring flow rates and pressures, for blood analysis or for delivering other percutaneous tools or devices to the vessel or as an inflation lumen for an occlusion balloon.

It is to be understood that in the various embodiments of the present invention, the expanded member does not require constant contact with the vessel walls to provide the required support. For example, the diameter of the expanded member may be less than the diameter of the vessel so that the expanded member only contacts the vessel wall when the vessel begins to collapse. Patency is considered to be maintained as long as the support device keeps the vessel open to a degree which is sufficient to maintain continuous flow.

To avoid causing turbulence or other undesirable blood flow effects within the vessel, and to optimize flow in the vessel it may be desirable to substantially match the diameter of the expanded member to the diameter of the vessel. Alternatively the expandable member may be shaped, e.g. as a coil or helix, to have minimal effect on the flow in the vessel.

In one embodiment, the expandable member may have a slightly larger expanded diameter than the relaxed vessel to create an anchoring effect. Depending on the size of the outflow vessel from which blood and perfusate is collected from the target region, there may be a natural tendency for the collection catheter tip to move about and contact the vessel, thus increasing the risk of vessel collapse or invagination of the catheter tip into the vessel wall. This can cause pooling of fluid in the isolated target region and may cause serious and permanent damage to the organ or region of the patient being treated. Use of a support structure in conjunction with the collection catheter to maintain patency of the outflow vessel, in accordance with embodiments of the present invention can minimize the risk of these complications eventuating. Thus, a collection catheter associated with the expanding member can be retained in position during fluid collection. This minimizes movement of the catheter tip, ensures that it is substantially centered relative to the vessel walls and improves withdrawal of fluid out of the vessel via the catheter collection opening.

At completion of the procedure, it is desirable that the expanded member is collapsed or compressed and recaptured, preferably in the catheter from which it was deployed. This facilitates removal of the support device from the patient. A reinforcing tip may be provided on the catheter end to strengthen it for recapture. Alternatively or additionally, the tip may be coated with a lubricant and/or material having a low coefficient of friction to facilitate smooth recapture of the expandable member. The catheter may also have an internal coating of lubricant and/or a material having a low coefficient of friction to assist translation of support device along its interior during delivery and removal of the device from the patient.

Although the present invention has been described in terms of the presently preferred embodiments, it is to be understood that the disclosure is not to be interpreted as limiting. Various alterations and modifications will no doubt become apparent to those skilled in the art after having read the above disclosure and it is intended that the present disclosure be interpreted as covering all alterations and modifications as fall within the true spirit and scope of the invention.

EXAMPLES

Example 1

Effect of support device on flow rates and pressures achievable during recirculation in sheep right hepatic vein, cephalic vein, coronary sinus and renal vein during recirculation.

A 0.014" diameter superelastic nitinol wire stem of 1.35 m length was used, coupled to an expandable member having 6 pre-shaped elliptical loop portions welded to the stem. A 0.024" OD atraumatic tip of 2 cm length attached to the distal end of the expandable member was used to position the device in the blood vessel. A balloon occlusion catheter was positioned in the vessel and the expandable member deployed at the tip of the catheter. The balloon was inflated to isolate and capture flows in the vessel and the catheter was connected to a standard extracorporeal circuit for blood circulation.

TABLE 1

Perfusion of the right hepatic and cephalic veins.

| Flow | pressure (mmHg) | | | |
|---|---|---|---|---|
| | right hepatic vein | | cephalic vein | |
| (mL/min) | device | no device | device | no device |
| 20 | | | | −200 |
| 40 | −10 | −13 | −11 | ↓ |
| 60 | −20 | −19 | −18 | no flow |
| 80 | | −30 | −23 | achievable |
| 100 | −30 | −47 | −32 | |
| 120 | −40 | −75 | −43 | |

TABLE 1-continued

Perfusion of the right hepatic and cephalic veins.

| Flow | pressure (mmHg) | | | |
|---|---|---|---|---|
| | right hepatic vein | | cephalic vein | |
| (mL/min) | device | no device | device | no device |
| 140 | −48 | −96 | −60 | |
| 160 | −60 | −112 | −71 | |
| 180 | −75 | −142 | −97 | |
| 200 | −94 | | −139 | |
| 220 | −115 | | | |
| 250 | −200 | | | |
| 220 | ↓ | | | |
| 200 | −92 | | | |
| 180 | | | ↓ | |
| 160 | | −115 | ↓ | |
| 140 | | | −180 | |

(Bold values indicate cavitation has occurred)

TABLE 2

Perfusion of coronary sinus and renal vein.

| RPM | pressure (mmHg) coronary sinus | | RPM | pressure (mmHg) renal vein | |
|---|---|---|---|---|---|
| | device | no device | | device | no device |
| 30 | −7 | −8 | 30 | | |
| 40 | −19 | −30 | 40 | | −200 |
| 50 | −33 | −45 | 50 | | no flow |
| 60 | −52 | −106 | 60 | | achievable |
| 70 | −67 | −154 | 70 | | |
| 80 | −84 | −203 | 80 | | |
| 90 | −137 | | 90 | | |
| 100 | −192 | | 100 | 18 | |
| 90 | −137 | | 150 | −14 | |
| 80 | | | 200 | −30 | |
| 70 | | | 250 | −55 | |
| 60 | ↓ | | 300 | −80 | |
| | no recovery | | 350 | | |
| | | | 400 | −120 no cavitation | |

(Bold values indicate cavitation has occurred)

Negative pressures were observed in perfusion lines draining the coronary sinus, renal vein, right hepatic vein and cephalic vein during recirculation both with and without a support device. These data show that cavitation is prevented at certain pressures in the vessels tested where a support device is used, but is not prevented where the support device is absent in the vessel at those pressures. Although cavitation may occur even with the support device, it occurs at higher flows. Also, cavitation ceases sooner where the support device was employed allowing flow to return to normal. In the coronary sinus, recovery from cavitation was not possible without the support device, emphasizing the importance of the device in the procedure. The data further demonstrates that vessel collapse can be irreversible in the absence of a support structure. However, where a support structure is present, the vessel collapse may be reversed by increasing pressure in the vessel or by slowing or reversing the flow rate of fluid through the vessel.

More specifically, considering the data for the right hepatic vein, flow rates of up to 250 mL per minute may be achieved before cavitation occurs where a support device is present in the vessel. Under the same conditions but where there is no support device, flow rates of only up to 180 mL per minute are possible. A more striking example of the advantages of the support device is seen for the cephalic vein where no flow is achievable without the device. When the vessel wall is supported by the device flow rates of up to 200 mL per minute are noted before cavitation occurs. When the vessel wall is supported flow rates of up to 200 mL per minute are noted before cavitation occurs.

The invention claimed is:

1. A method for percutaneously removing a fluid from a blood vessel, the method comprising:
   a) percutaneously positioning a collection catheter retrograde to blood flow within a vessel, the collection catheter defining a collection lumen in fluid communication with a collection opening located at a distal tip of the collection catheter, the collection catheter including an occlusion member capable of expansion and substantially occluding flow through the blood vessel during use, the occlusion member being disposed about the collection catheter and located proximal to the collection opening located at the distal tip of the collection catheter;
   b) extending a non-occlusive supporting device including a plurality of expandable members from substantially within the collection lumen of the collection catheter to a position at least partially external to the collection opening of the collection catheter, wherein the extending includes a radial expansion of the expandable members to a size having an outer peripheral dimension, the outer peripheral dimension being greater than an outer diameter of the distal tip of the collection catheter, and wherein the expansion of the expandable members prevents collapse of the blood vessel during a subsequent operation of a collection device connected to the collection catheter;
   c) expanding the occlusion member so as to substantially occlude retrograde blood flow within the vessel;
   d) removing a fluid from the blood vessel through the collection opening and the collection lumen of the collection catheter;
   e) contracting the occlusion member so as to re-establish retrograde blood flow within the vessel;
   f) withdrawing the non-occlusive supporting device from the extended position, through the collection opening, to a position within the collection lumen; and
   g) removing the collection catheter.

2. The method of claim 1, wherein the outer peripheral dimension is greater than an inside diameter of the blood vessel so as to anchor the non-occlusive supporting device at a fixed location within the blood vessel.

3. The method of claim 1, wherein the non-occlusive supporting device further comprises a flexible atraumatic guiding tip located distal of the radially expandable members.

4. The method of claim 3, wherein the non-occlusive support device and the flexible atraumatic guiding tip are connected via a guide wire, wherein the flexible atraumatic guiding tip is located at a distal end of the guide wire, and wherein the non-occlusive support device is located proximally, and adjacent to, the distal end of the guide wire.

5. The method of claim 4, wherein the non-occlusive supporting device is integrally formed with the guide wire.

6. The method of claim 4, wherein each of the plurality of radially expandable members of the non-occlusive support device comprises a distal portion connected to a distal portion of the guide wire, and a proximal portion wherein the proximal portion is connected to a distal portion of the collection catheter.

7. The method of claim 1, wherein the blood vessel includes a vein.

8. The method of claim 7, wherein the vein is associated with an organ selected from the group consisting of a heart, lungs, liver, kidney, brain, intestine, testicle, ovary, spleen, stomach, prostate, and pancreas.

9. The method of claim 1, wherein the blood vessel includes the coronary sinus.

10. The method of claim 1, wherein the fluid comprises at least one of a therapeutic and a diagnostic agent.

11. The method of claim 1, wherein the fluid comprises contrast media.

12. The method of claim 1, wherein the outer peripheral dimension is less than an inside diameter of the blood vessel.

13. The method of claim 1, wherein the outer peripheral dimension is at least one of greater than and equal to an inside diameter of the blood vessel.

* * * * *